United States Patent [19]

Dunaway

[11] Patent Number: 5,717,144

[45] Date of Patent: Feb. 10, 1998

[54] COLLAPSIBLE CONTAINER TEST FIXTURE

[75] Inventor: David Dunaway, Danville, Ala.

[73] Assignee: Edward S. Robbins, III, Muscle Shoals, Ala.

[21] Appl. No.: 654,878

[22] Filed: May 29, 1996

[51] Int. Cl.⁶ .................................................. G01N 3/08
[52] U.S. Cl. ............................. 73/818; 73/849; 73/821
[58] Field of Search .................................. 73/788, 790, 7, 73/818, 821, 813, 849, 851, 817

[56] References Cited

U.S. PATENT DOCUMENTS

| | | | |
|---|---|---|---|
| 3,443,423 | 5/1969 | Lou Ma | 73/821 |
| 3,628,379 | 12/1971 | Bobunovic | 73/817 |
| 4,046,000 | 9/1977 | Watkins et al. | 73/817 |
| 4,697,457 | 10/1987 | Fochtman | 73/820 |
| 4,807,465 | 2/1989 | Bolzlakis et al. | 73/821 |
| 5,226,551 | 7/1993 | Robbins, III | 220/8 |
| 5,417,337 | 5/1995 | Robbins, III | 220/8 |

Primary Examiner—George M. Dombroske
Assistant Examiner—Max H. Noori
Attorney, Agent, or Firm—Nixon & Vanderhye P.C.

[57] ABSTRACT

Apparatus for testing the collapsibility of a plastic container, the container having a bottom, a peripheral side wall and an upper opening, the side wall formed with at least one peripheral fold line which, upon compression, facilitates telescoping of one portion of the container side wall into another portion of the container side wall, the apparatus comprising a base supporting a platform sized to receive a bottom portion of a container; a tool platen supported above the platform for reciprocating movement toward and away from the platform, the platen mounting a tool sized and shaped to engage the upper opening of the container; and a force gauge operatively attached to the platform for measuring force required to move the container from an upright, extended condition to a collapsed condition.

17 Claims, 4 Drawing Sheets

COLLAPSIBLE CONTAINER TEST FIXTURE

This invention relates to a test fixture for validating a collapsible container design and, more specifically, to a test fixture which, in one exemplary use, compresses a collapsible container side wall from an extended position to a collapsed position, and which measures the force required to do so.

BACKGROUND

Collapsible plastic container or bottle constructions are disclosed in commonly owned U.S. Pat. Nos. 5,226,551 and 5,417,337, the subject matter of which is incorporated herein by reference. Such containers include one or more peripheral fold lines in the side wall of the container which facilitate a collapsing or folding action of the sidewall. More specifically, one axial portion of the side wall reverse folds into another axial portion of the side wall, thereby reducing the overall height of the container by a substantial margin. This is particularly useful for shipping and storing efficiencies. Such containers may include a thick/thin/thick side wall configuration as disclosed in U.S. Pat. Nos. 5,226,551 and 5,417,337, but the fixture may be utilized with other collapsible container designs as well.

In any case, during the development of such containers, it is necessary to test various side wall configurations, wall thickness dimensions and materials to determine the overall combination of design criteria best suited to a particular container application. The present invention has for its principal objective a simple, easy to use yet precise fixture which enables the container designer to identify optimum container configurations. It should be appreciated, however, that the fixture has other uses not necessarily related to that which is described herein.

In the exemplary embodiment, a test fixture is provided which includes a tool plate movable toward and away from a platform used to support the workpiece, in this case, a collapsible container of the type described above. The tool plate moves along a pair of guide rods, and is driven by means of a commercially available electric cylinder. The latter includes an axially movable output rod operably connected to the tool plate. Associated controls permit the stroke length and speed of the output rod and tool plate to be carefully controlled. The container supporting platform is itself operably connected to a commercially available force gauge which allows the operator to determine the force necessary to move the container from an upright extended position to a collapsed position.

The apparatus also permits fatigue cycle testing of the container, and in this regard the tool plate can be modified to enable pulling of the container from the collapsed to the extended position, again with the pulling force monitored. In this way, the viability of various materials, side wall configurations and wall thicknesses for various container constructions can be determined with great accuracy.

Accordingly, in its broader aspects, the present invention relates to apparatus for testing the collapsibility of a plastic container, the container having a bottom, a collapsible peripheral side wall and an upper opening, the apparatus comprising a base supporting a platform sized to receive a bottom portion of a container; a tool platen supported above the platform for reciprocating movement toward and away from the platform, the platen mounting a tool sized and shaped to engage the upper opening of the container; and a force gauge operatively attached to said platform for measuring force required to move the container from an upright, extended condition to a collapsed condition.

In another aspect, the invention relates to a compression and tension apparatus comprising a base; a plate mounted on the base; the plate supporting a platform movable relative to the plate and sized to receive a workpiece; a tool platen supported above the platform for reciprocating movement toward and away from the platform, the platen mounting a tool sized and shaped to engage the workpiece; and a force gauge supported by the plate and operatively attached to the platform for measuring a tension or compression force applied to the workpiece.

Other objects and advantages of the present invention will become apparent from the detailed description which follows.

DETAILED DESCRIPTION OF THE DRAWINGS

Figure 1:
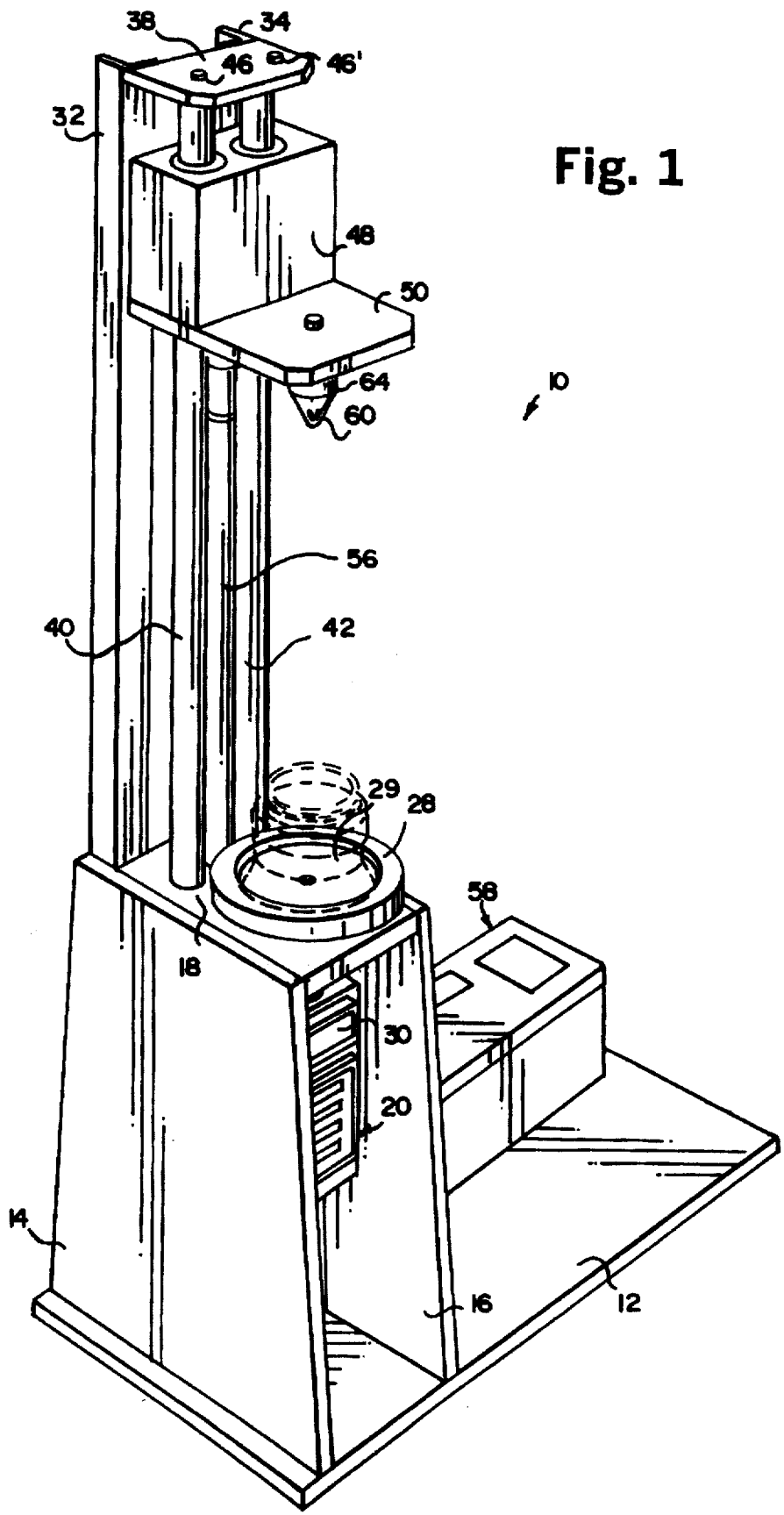
FIG. 1 is a perspective view of a test fixture in accordance with an exemplary embodiment of the invention.
Figure 2:
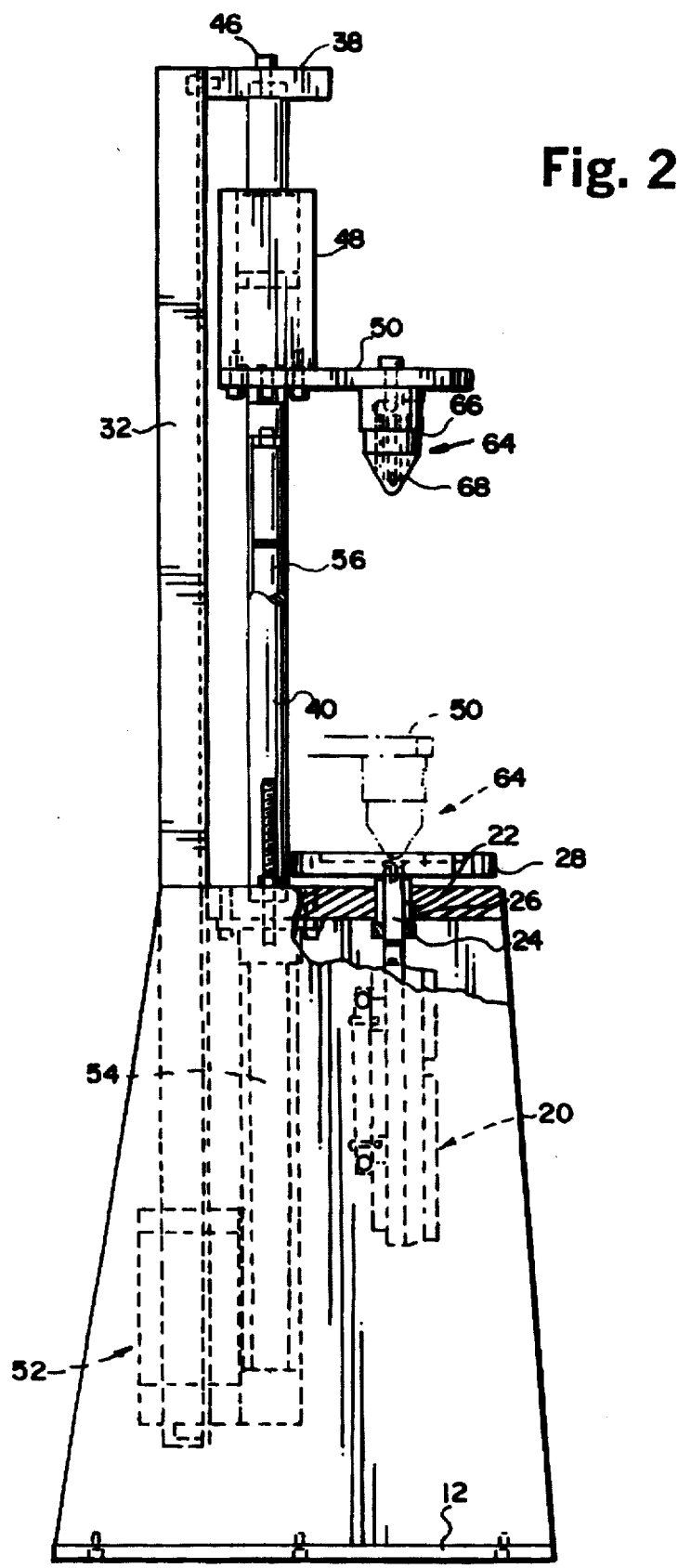
FIG. 2 is a side elevation of the fixture shown in FIG. 1, partly broken away and partly in section.

With reference now to FIG. 1, the test fixture 10 includes a lower base plate 12 which supports a pair of standards 14, 16 which are connected at their upper ends by an intermediate horizontal plate 18. The plate 18 supports a force gauge 20 suspended below the plate 18 by means of a combined bearing and retainer ring 22 and a collar 24 (see FIG. 2). The input shaft 26 of the force gauge extends upwardly through the plate 18 where it supports a container holder 28. The holder 28 may include a recess 29, sized to receive the bottom portion of a container or bottle. The force gauge 20 may be one commercially available under the name Ametek Accu Force III (#AF3100), but other comparable gauges may be used as well.

It will be appreciated that any pushing or pulling force exerted on the container holder 28 will be transmitted through the holder 28 to the force gauge via input shaft 26 and displayed on the face 30 of the gauge in grams/kilograms, ounces, pounds or newtons.

Figure 3:
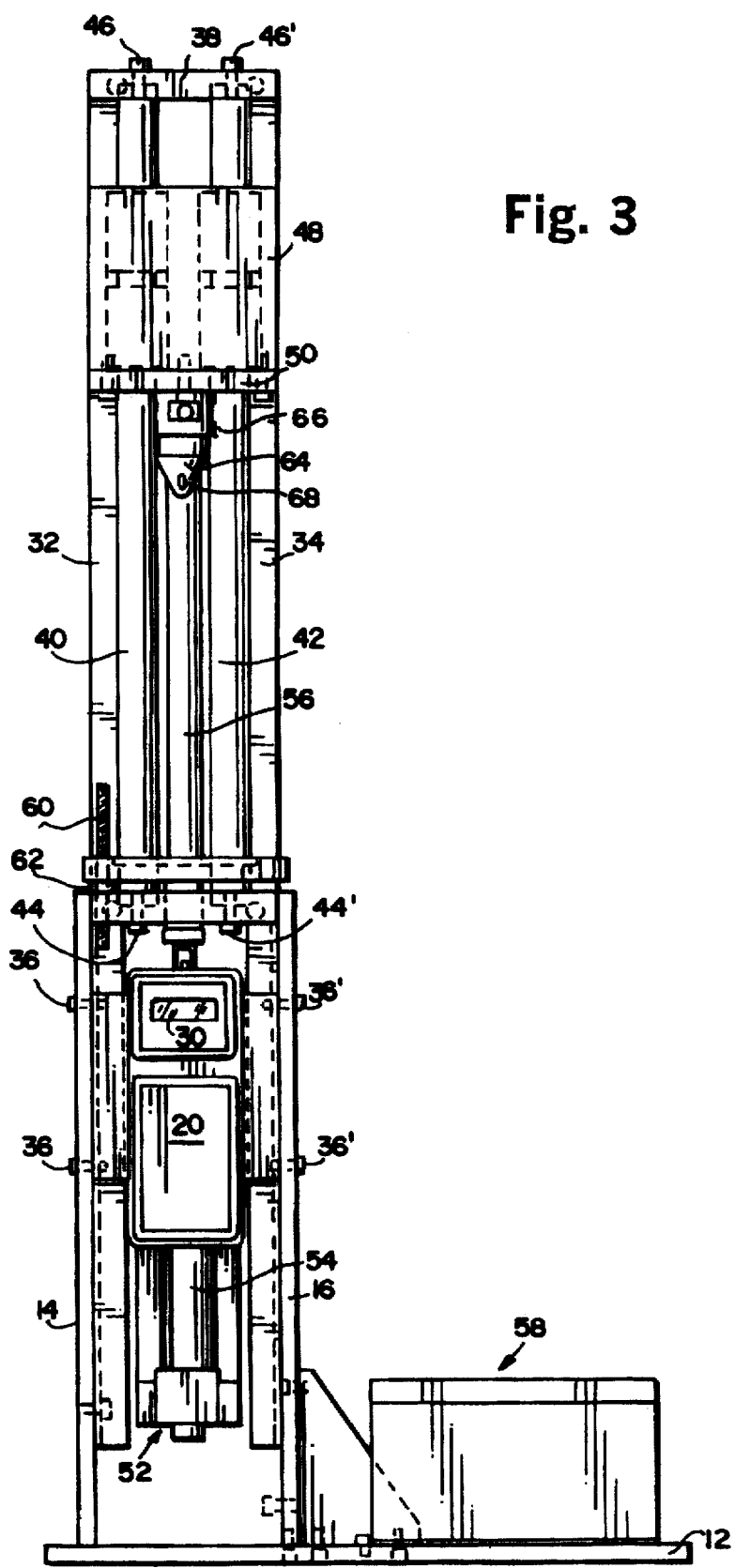
FIG. 3 is a front elevation of the test fixture shown in FIG. 1.
Figure 4:
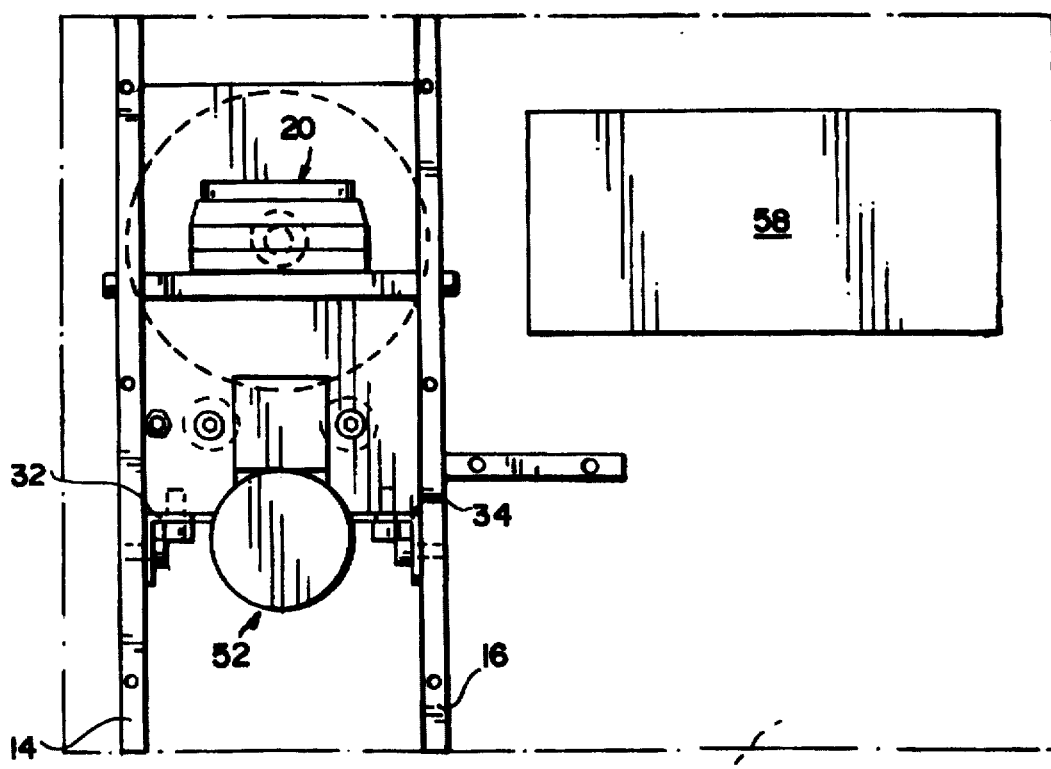
FIG. 4 is a bottom plan view of the test fixture shown in FIG. 1.
Figure 5:
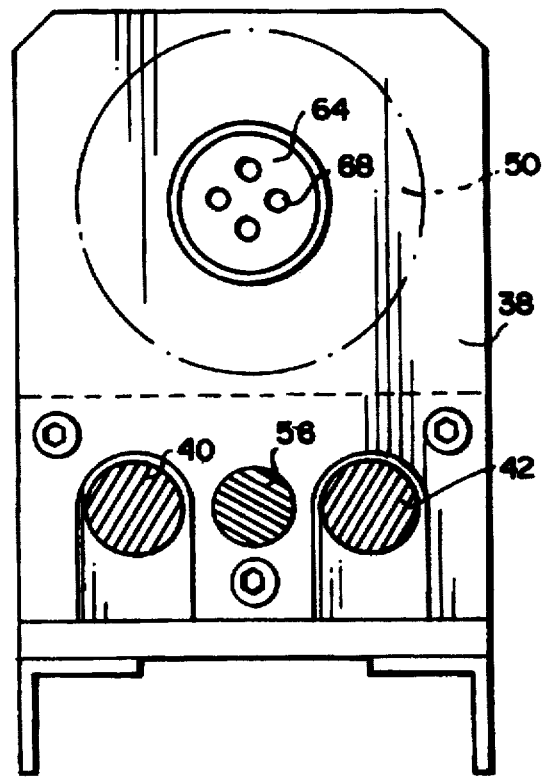
FIG. 5 is a section taken along line A—A of FIG. 2.

A pair of vertical angles 32, 34 extend in parallel relationship from the standards 14, 16, respectively, to which they are secured by bolts 36, 36' or other suitable fasteners (shown only in FIG. 3). These angles are joined at their uppermost edges by a top plate 38 which also extends forwardly of the angles 32, 34, as best seen in FIG. 1.

A pair of guide rods 40, 42 are secured to the intermediate plate 18 by bolts 44, 44' (shown only in FIG. 3), and extend in parallel to the top plate 38 to which they are secured by bolts 46, 46'. A bearing block 48, supporting a tool plate 50, is slidably mounted on the guide rods 40, 42 for movement toward and away from the container holder plate 28. Movement of the bearing block is controlled by a servo electric actuator, preferably an electric cylinder such as the IDC Model #NH102B-MF1-MT1-Q-Z, but other comparable actuators may be used. The cylinder generally designated by numeral 52, is mounted between the standards 14, 16 behind the force gauge 20. The output tube 54 of the cylinder is attached to an extension rod 56 extending upwardly between the guide t rods 42, 44 and connected to the bearing block 48. While the construction of the commercially available electric cylinder need not be described in detail, those of ordinary skill in the art will appreciate that when power is supplied, the cylinder motor, through either a timing belt, gear drive or direct coupling, rotates an acme or ball screw, thus causing the output tube 54 (and hence, rod 56 and bearing block 48) to move axially. As a result, the tool plate 50 is movable toward and away from a container mounted or located on the holder 28.

Movement of the cylinder output tube 54 is controlled by any suitable controller, for example, an IDS Model #H3851 Controller, shown generally at 58. The controller 58 is mounted on the base plate 12 and is electrically connected to the cylinder 52 in conventional fashion. The user may program the controller to set values for acceleration, deceleration and velocity, with the latter set in terms of percent of a top speed of 30 in./sec. The stroke distance of the tool plate 50 may also be set, depending on the type and size of container being tested.

With reference again to FIG. 2, a mechanical stop in the form of a threaded rod 60 may be used to halt the tool plate 50 at selected locations and to record peak forces at those locations. The rod is threadably secured in the platform 18 and can be axially adjusted with the aid of locking nut 62. The stop is also employed to prevent any overtravel of the tooling past the fully collapsed position of the container or bottle.

In the exemplary embodiment, an end plug 64 is employed as the tool on the tool plate 50. This plug 64 is sized and shaped to project into the ID of a plastic container or bottle neck, until the tool flange 66 seats on the upper edge of the container surrounding the discharge opening. By applying compressive forces to the container in this manner, the container can be collapsed in accordance with the side wall design, and the force necessary to effect the collapse is displayed on the screen 30 of the gauge 20. Vent holes 68 in the plug 64 permit air to escape from the container interior as it is collapsed. Typically, the apparatus is programmed to have the tool or end plug 64 collapse the container or bottle to a desired height and then return to its original position near the upper end of guide rods 40, 42.

It will be appreciated that the container, if desired, may be fixed to the holder 28 (by any suitable fasteners), so that, with the appropriate plug tool, the container can be pulled from a collapsed position to an extended position, again with the force necessary to do so displayed in the gauge screen 30. The consistency and accuracy of the apparatus has proven very successful and has enabled many positive design changes to be identified and subsequently implemented.

It will be appreciated that the tool shape may be modified to suit various container shapes and sizes. Various fatigue cycling tests can also be carried out on plastic containers, bottles or other workpieces. Moreover, the apparatus described herein has applicability in various other testing programs not necessarily related to collapsible containers.

For example, with appropriate tooling, some hot stamping operations may be carried out with the apparatus described herein, with stamping forces displayed on the face gauge.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. Apparatus for testing the collapsibility of a plastic container, the container having a bottom, a collapsible peripheral side wall and an upper opening, the apparatus comprising:

a base;

a plate mounted on said base;

said plate supporting a container holder having a recess sized and shaped to receive a bottom portion of a container;

a tool platen supported above said container holder for reciprocating movement toward and away from said container holder, said platen mounting a tool sized and shaped to engage the upper opening of the container;

a force gauge supported by said plate and operatively attached to said container holder for measuring force required to move the container from an upright, extended condition to a collapsed condition;

a drive for moving said tool platen at a predetermined speed toward and away from said container holder; and controls associated with said drive for setting said predetermined speed and for setting a stroke length for said tool platen, said stroke set to achieve a predetermined collapsed height for the container.

2. A compression and tension apparatus comprising:

a base;

a plate mounted on said base;

said plate supporting a workpiece holder movable relative to said plate and sized to receive a workpiece, said workpiece holder including means to secure the workpiece to the workpiece holder to thereby permit compression and tension forces to be applied to the workpiece;

a tool platen supported above said workpiece holder for reciprocating movement toward and away from said workpiece holder, said platen mounting a tool sized and shaped to engage said workpiece; and a force gauge supported by said plate and operatively attached to said workpiece for measuring the tension and compression forces applied to the workpiece, depending on direction of movement of said tool platen, wherein said force gauge is located below said plate, and wherein a shaft extends between said workpiece holder and said force gauge, through said plate.

3. The apparatus of claim 2 wherein said fixed plate includes an adjustable stop for limiting downward movement of said tool plate.

4. The apparatus of claim 1 wherein said drive comprises a servo electric actuator.

5. The apparatus of claim 1 wherein said plate supports a pair of upstanding guide rods and wherein said tool platen is mounted for sliding motion on said guide rods.

6. The apparatus of claim 5 wherein said force gauge is located below said plate, and wherein a shaft extends between said container holder and said force gauge, through said plate.

7. The apparatus of claim 1 wherein said tool includes a cylindrical body portion and a tapered nose portion.

8. The apparatus of claim 5 wherein said tool platen includes a plate extending horizontally from a guide block, said guide block having a pair of through holes which receive said guide rods.

9. The apparatus of claim 8 and including a drive rod extending between said guide block and said drive.

10. The apparatus of claim 6 wherein said fixed plate includes an adjustable stop for limiting downward movement of said tool plate.

11. The apparatus of claim 7 wherein said tool includes at least one aperture for venting air inside the container as the container is moved to the collapsed condition.

12. The apparatus of claim 2 wherein said plate supports a pair of upstanding guide rods and wherein said tool platen is mounted for sliding motion on said guide rods.

13. The apparatus of claim 2 and including a drive for moving said tool platen at a predetermined speed toward and away from said platform.

14. The apparatus of claim 13 and including controls associated with said drive for setting said predetermined speed and for setting a stroke length for said tool platen.

15. The apparatus of claim 2 wherein said drive comprises a servo electric actuator.

16. The apparatus of claim 12 wherein said tool platen includes a plate extending horizontally from a guide block, said guide block having a pair of through holes which receive said guide rods.

17. The apparatus of claim 12 and including a drive rod extending between said guide block and said drive.

* * * * *